(12) United States Patent
Avey

(10) Patent No.: US 8,340,950 B2
(45) Date of Patent: Dec. 25, 2012

(54) DIRECT TO CONSUMER GENOTYPE-BASED PRODUCTS AND SERVICES

(75) Inventor: Linda S. Avey, Los Gatos, CA (US)

(73) Assignee: Affymetrix, Inc., Santa Clara, CA (US)

( * ) Notice: Subject to any disclaimer, the term of this patent is extended or adjusted under 35 U.S.C. 154(b) by 1207 days.

(21) Appl. No.: 11/672,849

(22) Filed: Feb. 8, 2007

(65) Prior Publication Data

US 2008/0004848 A1    Jan. 3, 2008

Related U.S. Application Data

(60) Provisional application No. 60/772,109, filed on Feb. 10, 2006.

(51) Int. Cl.
    *G06G 7/58* (2006.01)
(52) U.S. Cl. .......................................................... 703/11
(58) Field of Classification Search ...................... 703/11
    See application file for complete search history.

(56) References Cited

U.S. PATENT DOCUMENTS

| | | |
|---|---|---|
| 2002/0128860 A1 | 9/2002 | Leveque et al. |
| 2003/0046110 A1 | 3/2003 | Gogolak |
| 2003/0104453 A1 | 6/2003 | Pickar et al. |
| 2003/0208454 A1 | 11/2003 | Rienhoff, Jr. et al. |
| 2008/0131887 A1 | 6/2008 | Stephan et al. |
| 2008/0261220 A1* | 10/2008 | Cracauer et al. .................. 435/6 |

FOREIGN PATENT DOCUMENTS

WO    WO2008/067551    6/2008

* cited by examiner

*Primary Examiner* — Jerry Lin
(74) *Attorney, Agent, or Firm* — Affymetrix, Inc.

(57) ABSTRACT

In one embodiment, a method of providing genotype-based information is described that comprises receiving one or more genotype calls that each identify a fraction of an individuals' genetic composition; assigning an electronically identifiable identifier for each genotype call; and generating a customized set of information using one or more of the identifiers.

20 Claims, 4 Drawing Sheets

DIRECT TO CONSUMER GENOTYPE-BASED PRODUCTS AND SERVICES

PRIORITY CLAIM

This application claims priority to provisional application Nos. 60/772,109 filed Feb. 10, 2006 which is incorporated herein by reference in its entirety for all purposes.

BACKGROUND

1. Field of the Invention

The present invention relates to the field of bioinformatics, genetic information and online marketing. In particular, the present invention relates to computer systems, methods, and products for providing direct to consumer genotype-based products and services typically provided over networks such as the Internet. In particular the present invention relates to generating one or more electronic identifiers associated with one or more genetic markers such as single nucleotide polymorphisms (commonly referred to as SNP's) and/or sequence calls or signatures of a plurality of sequence calls. The electronic identifiers may be associated with one or more "lookup" tables or other similar types of data structure that enable the identifiers to be queried and associated with search results and/or one or more related products or services.

2. Related Art

Research in molecular biology, biochemistry, and many related health fields increasingly requires organization and analysis of complex data generated by new experimental techniques. These tasks are addressed by the rapidly evolving field of bioinformatics. See, e.g., H. Rashidi and K. Buehler, Bioinformatics Basics: Applications in Biological Science and Medicine (CRC Press, London, 2000); Bioinformatics: A Practical Guide to the Analysis of Gene and Proteins (B. F. Ouelette and A. D. Baxevanis, eds., Wiley & Sons, Inc.; 2d ed., 2001), both of which are hereby incorporated herein by reference in their entireties. Broadly, one area of bioinformatics applies computational techniques to large genomic databases, often distributed over and accessed through networks such as the Internet, for the purpose of illuminating relationships among alternative splice variants, protein function, and metabolic processes.

SUMMARY OF THE INVENTION

Systems, methods, and products to address these and other needs are described herein with respect to illustrative, non-limiting, implementations. Various alternatives, modifications and equivalents are possible. For example, certain systems, methods, and computer software products are described herein using exemplary implementations for analyzing data from arrays of biological materials produced by Affymetrix® GeneChip® probe arrays. However, these systems, methods, and products may be applied with respect to many other types of probe arrays and, more generally, with respect to numerous parallel biological assays produced in accordance with other conventional technologies and/or produced in accordance with techniques that may be developed in the future. For convenience, the term "probe array" will generally be used broadly hereafter to refer to all of these types of arrays and parallel biological assays.

In one embodiment, a method of providing genotype-based information is described that comprises receiving one or more genotype calls that each identify a fraction of an individuals' genetic composition; assigning an electronically identifiable identifier for each genotype call; and generating a customized set of information using one or more of the identifiers.

It is also important to be able to relate databases containing genotypic information to the health assessment profiles or phenotypic databases of particular subjects. The presently preferred embodiments discussed below relate to the use of genomic analysis methods, such as the use of probe arrays, with subjects. Some analysis methods use genetic marker such as SNPs, STRs, copy number mutations or other polymorphisms.

The methods of the invention are particularly well suited for online advertising and connection between a subject or consumer and vendors of products or services targeted to particular genotypes. The present invention can also be useful in predictive diagnostics, novel therapeutics, nutritional therapies and community related information transmission for people with similar genotypes.

One preferred embodiment is a method of providing genotype-based information, comprising: receiving one or more genotype calls, wherein each genotype call identifies a fraction of an individuals genetic composition; assigning an identifier for each genotype call, wherein the identifier is electronically identifiable; and generating a customized set of information using one or more of the identifiers. In another preferred embodiment, the genotype calls are calls generated from biological probe arrays and are used to select products or services over a network. The products or services may be searched by using search terms such asphenotype, genotype, physical condition, qualities, traits, diseases, states, gene data, expression or protein information, location, community information, interests, habits, preferences, and allergies.

Another preferred embodiment is a method to automatically match genotyping information to commercial products or services, comprising, obtaining genotype information; assigning an electronic tag for each genotype call; storing the electronic tag in a database; and matching one or more electronic tags to commercial products or services over a network.

Another preferred embodiment is a system to automatically match genotyping information to commercial products or services, comprising, a computer having a database to store a plurality of genotype calls derived from an individual; an electronic tag for each genotype call; and a network to match the electronic tags to commercial products or services.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 160 appears first in FIG. 1). In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

DETAILED DESCRIPTION

Figure 1:
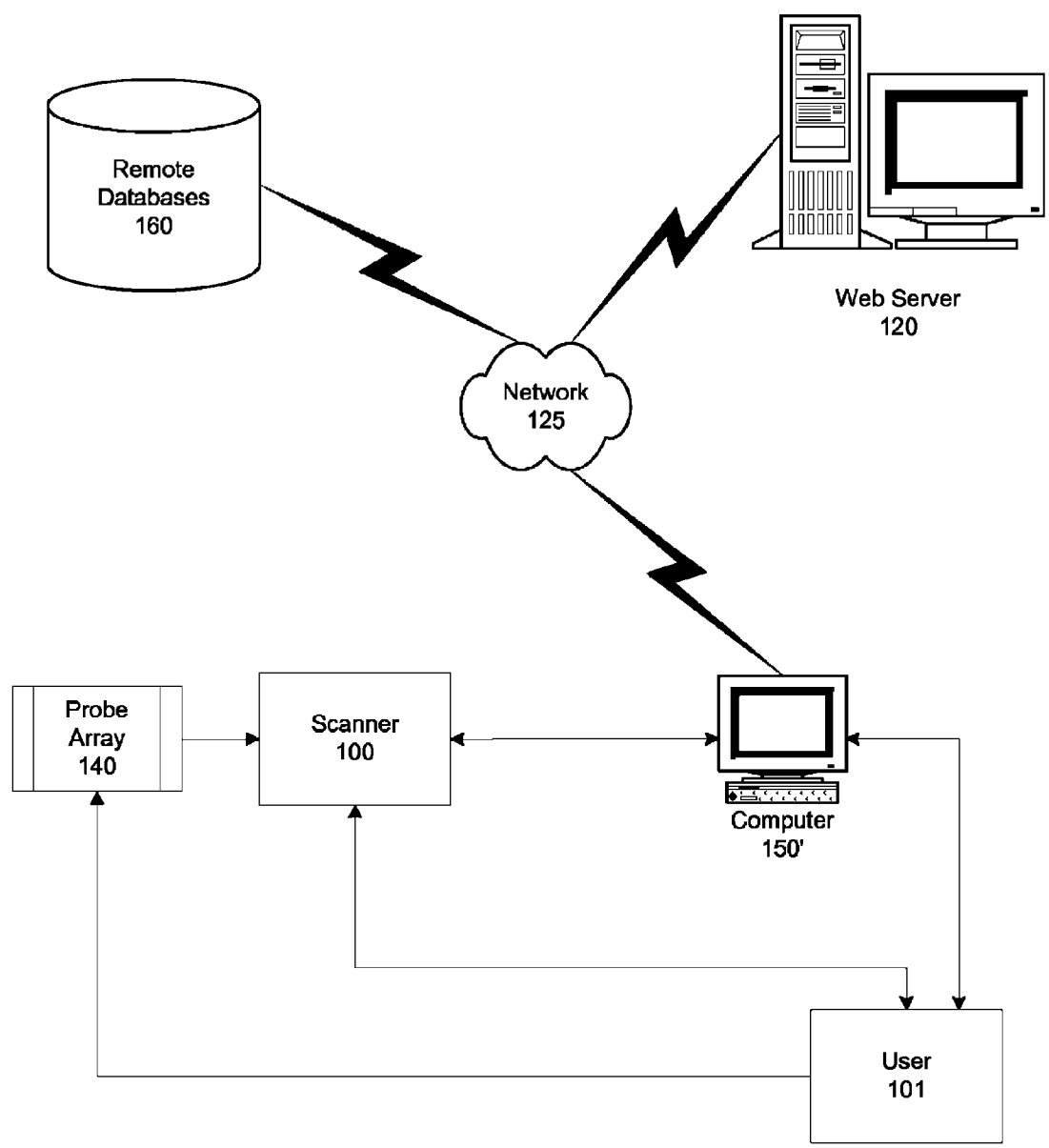
FIG. 1 is a functional block diagram of one embodiment of a web server in communication with remote databases and a computer over a network.

Associations of genotype or genetic sequence to various human traits and conditions are resulting from research studies enabled by the completion of the sequencing of the human genome. Direct-to consumer genotyping services offer individuals the ability to obtain their own genetic data, whether in the form of SNP genotyping or more comprehensive genome and/or mitochondrial DNA sequencing. The invention described here outlines the process of enabling electronic linkage of genotype or sequence data to known genetic associations.

Genotype or sequence data that has been generated for an individual on any platform or technology is stored in a database. Each genotype call or sequence datapoint for that individual is then assigned an electronic tag (for example, XML), creating a new field in the dataset with this code, or GenoTag. The GenoTag, or a set of GenoTags (called a GenoTag Signature), is then available for use as an electronic identifier during internet searches or other data mining purposes.

a) GENERAL

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W.H. Freeman Pub., New York, N.Y. and Berg et al. (2002) Biochemistry, 5th Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252, 743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,945,334, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285 (International Publication Number WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871, 928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592 and U.S. Ser. Nos. 09/916,135, 09/920,491 (U.S. Patent Application Publication 20030096235), 09/910,292 (U.S. Patent Application Publication 20030082543), and Ser. No. 10/013,598.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (United States Publication No. 20020183936), 10/065,856, 10/065,868, 10/328,818, 10/328,872, 10/423,403, and 60/482,389.

b) DEFINITIONS

The term "array" as used herein refers to an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The term "biopolymer" or "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a bioploymer is a "biomonomer".

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complex population or mixed population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "effective amount" as used herein refers to an amount sufficient to induce a desired result.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization conditions" as used herein will typically include salt concentrations of less than about 1M, more usually less than about 500 mM and preferably less than about 200 mM. Hybridization temperatures can be as low as 5.degree. C., but are typically greater than 22.degree. C., more typically greater than about 30.degree. C., and preferably in excess of about 37.degree. C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" 2nd Ed. Cold Spring Harbor Press (1989) which is hereby incorporated by reference in its entirety for all purposes above.

Hybridizations, e.g., allele-specific probe hybridizations, are generally performed under stringent conditions. For example, conditions where the salt concentration is no more than about 1 Molar (M) and a temperature of at least 25 degrees-Celsius (° C.), e.g., 750 mM NaCl, 50 mM NaPhosphate, 5 mM EDTA, pH 7.4 (5×SSPE) and a temperature of from about 25 to about 30° C.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (e.g., total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present.

Most preferably, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies.

The term "linkage disequilibrium or allelic association" as used herein refers to the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

The term "mixed population" as used herein refers to a complex population.

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library or array" as used herein refers to an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, Principles of Biochemistry, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "primer" as used herein refers to a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "search term" as used herein refers to one or more selection criteria. Example search terms are phenotype, genotype, physical condition, qualities, traits, diseases, states, gene data, expression or protein information, location, community information, interests, habits, preferences, allergies, and any other selectable criteria.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

As used herein, the term "hyperlink" refers to a navigational link from one document to another, or from one portion (or component) of a document to another. Typically, a hyperlink is displayed as a highlighted word or phrase that can be selected by clicking on it using a mouse to jump to the associated document or documented portion.

As used herein, the term "hypertext system" refers to a computer-based informational system in which documents (and possibly other types of data entities) are linked together via hyperlinks to form a user-navigable "web."

As used herein, the term "Internet" refers to any collection of networks using standard protocols. For example, the term includes a collection of interconnected (public and/or private) networks that are linked together by a set of standard protocols (such as TCP/IP, HTTP, and FTP) to form a global, distributed network. While this term is intended to refer to what is now commonly known as the Internet, it is also intended to encompass variations that may be made in the future, including changes and additions to existing standard protocols or integration with other media (e.g., television, radio, etc). The term is also intended to encompass non-public networks such as private (e.g., corporate) Intranets.

As used herein, the term "web site" refers to a computer system that serves informational content over a network using the standard protocols of the World Wide Web. Typically, a Web site corresponds to a particular Internet domain name and includes the content associated with a particular organization. As used herein, the term is generally intended to encompass both (i) the hardware/software server components that serve the informational content over the network, and (ii) the "back end" hardware/software components, including any non-standard or specialized components, that interact with the server components to perform services for Web site users.

As used herein, the term "HTML" refers to HyperText Markup Language that is a standard coding convention and set of codes for attaching presentation and linking attributes to informational content within documents. HTML is based on SGML, the Standard Generalized Markup Language. During a document authoring stage, the HTML codes (referred to as "tags") are embedded within the informational content of the document. When the Web document (or HTML document) is subsequently transferred from a Web server to a browser, the codes are interpreted by the browser and used to parse and display the document. Additionally, in specifying how the Web browser is to display the document, HTML tags can be used to create links to other Web documents (commonly referred to as "hyperlinks").

As used herein, the term "XML" refers to Extensible Markup Language, an application profile that, like HTML, is based on SGML. XML differs from HTML in that: information providers can define new tag and attribute names at will; document structures can be nested to any level of complexity; any XML document can contain an optional description of its grammar for use by applications that need to perform structural validation. XML documents are made up of storage units called entities, which contain either parsed or unparsed data. Parsed data is made up of characters, some of which form character data, and some of which form markup. Markup encodes a description of the document's storage layout and logical structure. XML provides a mechanism to impose constraints on the storage layout and logical structure, to define constraints on the logical structure and to support the use of predefined storage units. A software module called an XML processor is used to read XML documents and provide access to their content and structure.

As used herein, the term "HTTP" refers to HyperText Transport Protocol that is the standard World Wide Web client-server protocol used for the exchange of information (such as HTML documents, and client requests for such documents) between a browser and a Web server. HTTP includes a number of different types of messages that can be sent from the client to the server to request different types of server actions. For example, a "GET" message, which has the format GET, causes the server to return the document or file located at the specified URL.

As used herein, the term "URL" refers to Uniform Resource Locator that is a unique address that fully specifies the location of a file or other resource on the Internet. The general format of a URL is protocol://machine address:port/path/filename. The port specification is optional, and if none is entered by the user, the browser defaults to the standard port for whatever service is specified as the protocol. For example, if HTTP is specified as the protocol, the browser will use the HTTP default port of 80.

As used herein, the term "PUSH technology" refers to an information dissemination technology used to send data to users over a network. In contrast to the World Wide Web (a "pull" technology), in which the client browser should request a Web page before it is sent, PUSH protocols send the informational content to the user computer automatically, typically based on information pre-specified by the user.

As used herein, the term "communication network" refers to any network that allows information to be transmitted from one location to another. For example, a communication network for the transfer of information from one computer to another includes any public or private network that transfers information using electrical, optical, satellite transmission, and the like. Two or more devices that are part of a communication network such that they can directly or indirectly transmit information from one to the other are considered to be "in electronic communication" with one another. A computer network containing multiple computers may have a central computer ("central node") that processes information to one or more sub-computers that carry out specific tasks ("sub-nodes"). Some networks comprises computers that are in "different geographic locations" from one another, meaning that the computers are located in different physical locations (i.e., aren't physically the same computer, e.g., are located in different countries, states, cities, rooms, etc.).

C) EMBODIMENTS OF THE PRESENT INVENTION

The following are specifically preferred embodiments of the present invention. For example, they refer to preferred ways of acquiring genotyping information for their application in the present invention.

Probe Array 140: An illustrative example of probe array 140 is provided in FIG. 1. Descriptions of probe arrays are provided above with respect to "Nucleic Acid Probe arrays" and other related disclosure. In various implementations, probe array 140 may be disposed in a cartridge or housing such as, for example, the GeneChip® probe array available from Affymetrix, Inc. of Santa Clara Calif. Examples of probe arrays and associated cartridges or housings may be found in U.S. Pat. Nos. 5,945,334, 6,287,850, 6,399,365, 6,551,817, each of which is also hereby incorporated by reference herein in its entirety for all purposes. In addition, some embodiments of probe array 140 may be associated with pegs or posts, where for instance probe array 140 may be affixed via gluing, welding, or other means known in the related art to the peg or post that may be operatively coupled to a tray, strip or other type of similar substrate. Examples with embodiments of probe array 140 associated with pegs or posts may be found in U.S. patent Ser. No. 10/826,577, titled "Immersion Array Plates for Interchangeable Microtiter Well Plates", filed Apr. 16, 2004, which is hereby incorporated by reference herein in its entirety for all purposes.

Scanner 100: Labeled targets hybridized to probe arrays may be detected using various devices, sometimes referred to as scanners, as described above with respect to methods and apparatus for signal detection. An illustrative device is shown in FIG. 1 as scanner 100. For example, scanners image the targets by detecting fluorescent or other emissions from labels associated with target molecules, or by detecting transmitted, reflected, or scattered radiation. A typical scheme employs optical and other elements to provide excitation light and to selectively collect the emissions.

For example, scanner 100 provides a signal representing the intensities (and possibly other characteristics, such as color that may be associated with a detected wavelength) of the detected emissions or reflected wavelengths of light, as well as the locations on the substrate where the emissions or reflected wavelengths were detected. Typically, the signal includes intensity information corresponding to elemental sub-areas of the scanned substrate. The term "elemental" in this context means that the intensities, and/or other characteristics, of the emissions or reflected wavelengths from this area each are represented by a single value. When displayed as an image for viewing or processing, elemental picture elements, or pixels, often represent this information. Thus, in the present example, a pixel may have a single value representing the intensity of the elemental sub-area of the substrate from which the emissions or reflected wavelengths were scanned. The pixel may also have another value representing another characteristic, such as color, positive or negative image, or other type of image representation. The size of a pixel may vary in different embodiments and could include a 2.5 µm, 1.5 µm, 1.0 µm, or sub-micron pixel size. Two examples where the signal may be incorporated into data are data files in the form *.dat or *.tif as generated respectively by Affymetrix® Microarray Suite (described in U.S. patent application Ser. No. 10/219,882, which is hereby incorporated by reference herein in its entirety for all purposes) or Affymetrix® GeneChip® Operating Software (described in U.S. patent application Ser. No. 10/764,663, which is hereby incorporated by reference herein in its entirety for all purposes) based on images scanned from GeneChip® arrays, and Affymetrix® Jaguar™ software (described in U.S. patent application Ser. No. 09/682,071, which is hereby incorporated by reference herein in its entirety for all purposes) based on images scanned from spotted arrays. Examples of scanner systems that may be implemented with embodiments of the present invention include U.S. patent application Ser. Nos. 10/389,194; and 10/913,102, both of which are incorporated by reference above; and U.S. patent application Ser. No. 10/846,261, titled "System, Method, and Product for Providing A Wavelength-Tunable Excitation Beam", filed May 13, 2004; and U.S. patent application Ser. No. 11/260,617, titled "System, Method and Product for Multiple Wavelength Detection Using Single Source Excitation", filed Oct. 27, 2005, each of which is hereby incorporated by reference herein in its entirety for all purposes.

Computer 150: An illustrative example of computer 150 is provided in FIG. 1 and also in greater detail in FIG. 2. Computer 150 may be any type of computer platform such as a workstation, a personal computer, a server, or any other present or future computer. Computer 150 typically includes known components such as a processor 255, an operating system 260, system memory 270, memory storage devices 281, and input-output controllers 275, input devices 240, and display/output devices 245. Display/Output Devices 245 may include display devices that provides visual information, this information typically may be logically and/or physically organized as an array of pixels. A Graphical user interface (GUI) controller may also be included that may comprise any of a variety of known or future software programs for providing graphical input and output interfaces such as for instance GUI's 246. For example, GUI's 246 may provide one or more graphical representations on one or more display devices to a user, such as user 101, and also be enabled to process user inputs via GUI's 246 using means of selection or input known to those of ordinary skill in the related art.

It will be understood by those of ordinary skill in the relevant art that there are many possible configurations of the components of computer 150 and that some components that may typically be included in computer 150 are not shown, such as cache memory, a data backup unit, and many other devices. Processor 255 may be a commercially available processor such as an ITANIUM® or PENTIUM® processor made by Intel Corporation, a SPARC® processor made by Sun Microsystems, an ATHALON™ or OPTERON™ processor made by AMD corporation, or it may be one of other processors that are or will become available. Some embodiments of processor 255 may also include what are referred to as Multi-core processors and/or be enabled to employ parallel processing technology in a single or multi-core configuration. For example, a multi-core architecture typically comprises two or more processor "execution cores". In the present example each execution core may perform as an independent processor that enables parallel execution of multiple threads.

Processor 255 executes operating system 260, which may be, for example, a Windows®-type operating system (such as Windows XP) from the Microsoft Corporation; a Unix® or Linux-type operating system available from many vendors or what is referred to as an open source; another or a future operating system; or some combination thereof. Operating system 260 interfaces with firmware and hardware in a well-known manner, and facilitates processor 255 in coordinating and executing the functions of various computer programs that may be written in a variety of programming languages. Operating system 260, typically in cooperation with processor 255, coordinates and executes functions of the other components of computer 150. Operating system 260 also provides scheduling, input-output control, file and data management, memory management, and communication control and related services, all in accordance with known techniques.

System memory 270 may be any of a variety of known or future memory storage devices. Examples include any commonly available random access memory (RAM), magnetic medium such as a resident hard disk or tape, an optical medium such as a read and write compact disc, or other memory storage device. Memory storage devices 281 may be any of a variety of known or future devices, including a compact disk drive, a tape drive, a removable hard disk drive, flash memory, or a diskette drive. Such types of memory storage devices 281 typically read from, and/or write to, a program storage medium (not shown) such as, respectively, a compact disk, magnetic tape, removable hard disk, flash memory, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 270 and/or the program storage device used in conjunction with memory storage device 281.

In some embodiments, a computer program product is described comprising a computer usable medium having control logic (computer software program, including program code) stored therein. The control logic, when executed by processor 255, causes processor 255 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 275 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 275 could include controllers for any of a variety of known display devices for presenting information to a user, whether a human or a machine, whether local or remote. In the illustrated embodiment, the functional elements of computer 150 communicate with each other via system bus 290. Some of these communications may be accomplished in alternative embodiments using network or other types of remote communications.

Figure 2:
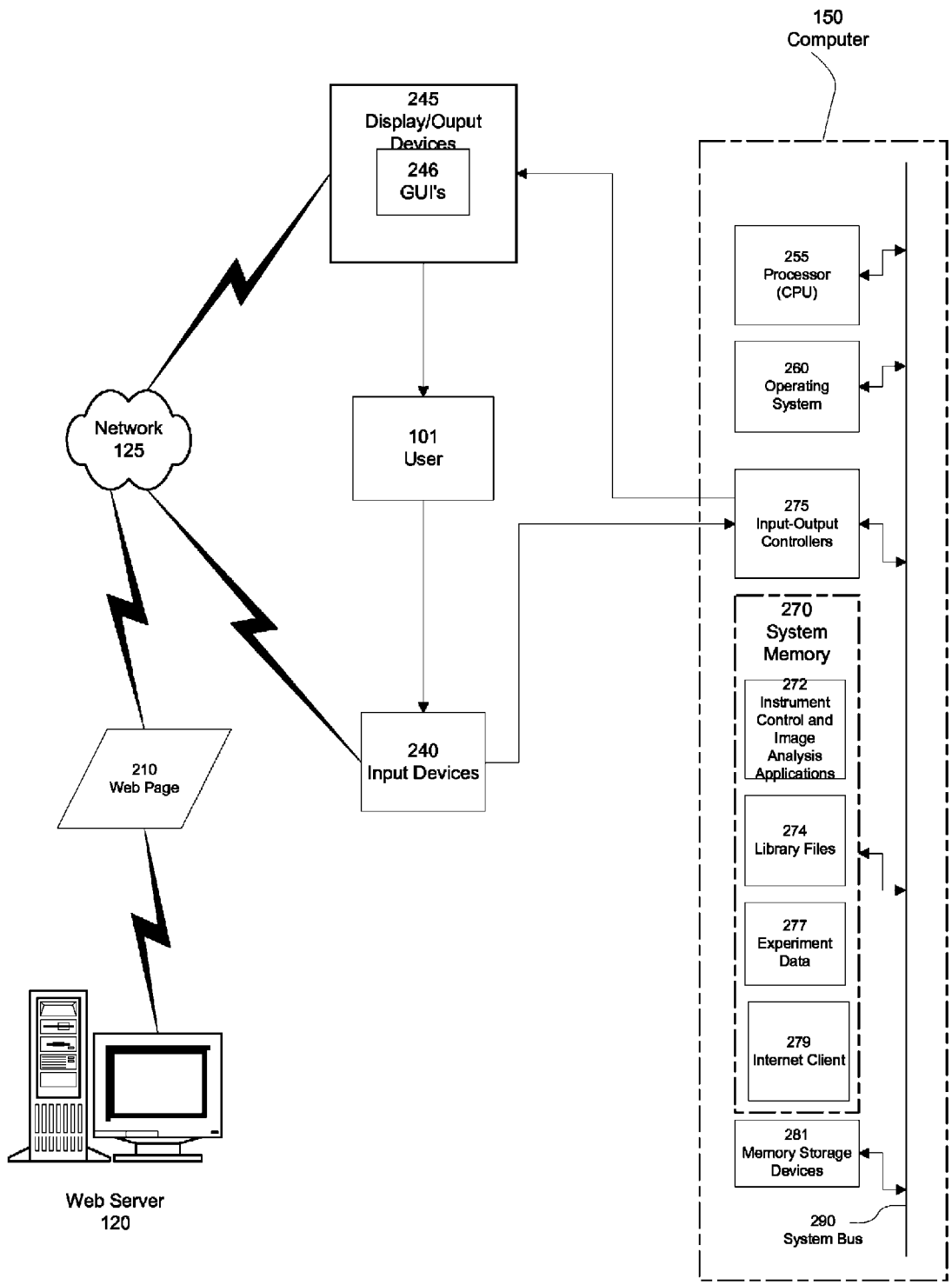
FIG. 2 is a functional block diagram of one embodiment of the computer of FIG. 1 comprising display devices that displays one or more web pages communicated from the web server over the network.

As will be evident to those skilled in the relevant art, instrument control and image processing applications 272, if implemented in software, may be loaded into and executed from system memory 270 and/or memory storage device 281. All or portions of applications 272 may also reside in a read-only memory or similar device of memory storage device 281, such devices not requiring that applications 272 first be loaded through input-output controllers 275. It will be understood by those skilled in the relevant art that applications 272, or portions of it, may be loaded by processor 255 in a known manner into system memory 270, or cache memory (not shown), or both, as advantageous for execution. Also illustrated in FIG. 2 are library files 274, experiment data 277, and internet client 279 stored in system memory 270. For example, experiment data 277 could include data related to one or more experiments or assays such as excitation wavelength ranges, emission wavelength ranges, extinction coefficients and/or associated excitation power level values, or other values associated with one or more fluorescent labels. Additionally, internet client 279 may include an application enabled to accesses a remote service on another computer using a network that may for instance comprise what are generally referred to as "Web Browsers". In the present example some commonly employed web browsers include Netscape® 8.0 available from Netscape Communications Corp., Microsoft® Internet Explorer 6 with SP1 available from Microsoft Corporation, Mozilla Firefox® 1.5 from the Mozilla Corporation, or other type of web browser currently known in the art or to be developed in the future. Also, in the same or other embodiments internet client 279 may include, or could be an element of, specialized software applications enabled to access remote information via a network such as network 125 such as, for instance, the GeneChip® Data Analysis Software (GDAS) package, GeneChip® Genotyping Analysis Software (GTYPE), GeneChip® Sequence Analysis Software (GSEQ), or Chromosome Copy Number Tool (CNAT) both available from Affymetrix, Inc. of Santa Clara Calif. that are each enabled to access information, and in particular probe array annotation information from the NetAffx™ web site hosted on one or more servers provided by Affymetrix, Inc.

Network 125 may include one or more of the many various types of networks well known to those of ordinary skill in the art. For example, network 125 may include a local or wide area network that employs what is commonly referred to as a TCP/IP protocol suite to communicate, that may include a network comprising a worldwide system of interconnected computer networks that is commonly referred to as the internet, or could also include various intranet architectures.

Instrument control and image processing applications 272: Instrument control and image processing applications 272 may be any of a variety of known or future image processing applications. Examples of applications 272 include Affymetrix® Microarray Suite, Affymetrix® GeneChip® Operating Software (hereafter to as GCOS), and Affymetrix® Jaguar™ software, noted above. Applications 272 may be loaded into system memory 270 and/or memory storage device 281 through one of input devices 240.

Embodiments of applications 272 include executable code being stored in system memory 270 of an implementation of computer 150. Applications 272 may provide a user interface for both the client workstation and one or more servers such as, for instance, GeneChip® Operating Software Server (GCOS Server) available from Affymetrix, Inc. Santa Clara, Calif. Applications 272 could additionally provide the user interface for one or more other workstations and/or one or more instruments. In the presently described implementation, the interface may communicate with and control one or more elements of the one or more servers, one or more workstations, and the one or more instruments. In the described implementation the client workstation could be located locally or remotely to the one or more servers and/or one or more other workstations, and/or one or more instruments. The user interface may, in the present implementation, include an interactive graphical user interface (generally referred to as a GUI), such as GUI's 246, that allow a user to make selections based upon information presented in the GUI. For example, applications 272 may provide GUI 246 that allows a user to select from a variety of options including data selection, experiment parameters, calibration values, probe array information. Applications 272 may also provide a graphical representation of raw or processed image data where the processed image data may also include annotation information superimposed upon the image such as, for instance, base calls, features of probe array 140, or other useful annotation information. Further examples of providing annotation information on image data are provided in U.S. Provisional Patent Application Ser. No. 60/493,950, titled "System, Method, and Product for Displaying Annotation Information Associated with Microarray Image Data", filed Aug. 8, 2003, which is hereby incorporated by reference herein in its entirety for all purposes.

In alternative implementations, applications 272 may be executed on a server, or on one or more other computer platforms connected directly or indirectly (e.g., via another network, including the Internet or an Intranet) to network 125.

Embodiments of applications 272 also include instrument control features. The instrument control features may include the control of one or more elements of one or more instruments that could, for instance, include elements of a fluid processing station, what may be referred to as an automatic cartridge or tray loader, one or more robotic elements, and scanner 100. The instrument control features may also be capable of receiving information from the one more instruments that could include experiment or instrument status, process steps, or other relevant information. The instrument control features could, for example, be under the control of or an element of the user interface. In the present example, a user may input desired control commands and/or receive the instrument control information via one of GUI's 246. Additional examples of instrument control via a GUI or other interface is provided in U.S. Provisional Patent Application Ser. No. 60/483,812, titled "System, Method and Computer Software for Instrument Control, Data Acquisition and Analysis", filed Jun. 30, 2003, which is hereby incorporated by reference herein in its entirety for all purposes.

In some embodiments, image data is operated upon by applications 272 to generate intermediate results. Examples of intermediate results include so-called cell intensity files (*.cel) and chip files (*.chp) generated by Affymetrix® GeneChip® Operating Software, GeneChip® Data Analysis Software (GDAS), GeneChip® Genotyping Analysis Software (GTYPE), or GeneChip® Sequence Analysis Software (GSEQ), or Affymetrix® Microarray Suite (as described, for example, in U.S. patent application Ser. Nos. 10/219,882, and 10/764,663, both of which are hereby incorporated herein by reference in their entireties for all purposes), all of which are hereby incorporated by reference herein in their entireties for all purposes). For convenience, the term "file" often is used herein to refer to data generated or used by applications 272 and executable counterparts of other applications, but any of a variety of alternative techniques known in the relevant art for storing, conveying, and/or manipulating data may be employed.

For example, applications 272 receives image data derived from a GeneChip® probe array and generates a cell intensity file. This file contains, for each probe scanned by scanner 100, a single value representative of the intensities of pixels measured by scanner 100 for that probe. Thus, in some embodiments the intensity value is a measure of the presence of a target DNA sequence that represents a particular SNP or sequence nucleotide, hybridized to a complementary probe sequence. Similarly, in some embodiments the intensity value is a measure of the abundance of labeled target mRNA sequences present in the sample that hybridized to the corresponding probe sequence. Many such probe sequences may be present in each probe feature, as a probe feature on a GeneChip® probe array may include, for example, millions of oligonucleotides designed to detect the target sequences.

As noted, another file illustratively assumed to be generated by applications 272 is a *.chp file. In the present example, applications 272 may include the Affymetrix® GeneChip® Operating Software, GeneChip® Data Analysis Software (GDAS), GeneChip® Genotyping Analysis Software (GTYPE), or GeneChip® Sequence Analysis Software (GSEQ) Applications 272 may derive genotype or mRNA expression calls from analysis of the *.cel file combined in some cases with information derived from lab data and/or library files 274 that specify details regarding the sequences and locations of probe features and controls. The resulting data stored in the chip file includes degrees of hybridization, absolute and/or differential (over two or more experiments) expression, genotype comparisons, detection of polymorphisms and mutations, and other analytical results.

In another example, in which applications 272 includes Affymetrix® Jaguar™ software operating on image data from a spotted probe array, the resulting spot file includes the intensities of labeled targets that hybridized to probes in the array. Further details regarding cell files, chip files, and spot files are provided in U.S. patent application Ser. Nos. 09/682, 074 incorporated by reference above, as well as 10/126,468; 10/657,481; 10/986,963; 11/157,768; and 09/682,098; which are hereby incorporated by reference herein in their entireties for all purposes. As will be appreciated by those skilled in the relevant art, the preceding and following descriptions of files generated by applications 272 are exemplary only, and the data described, and other data, may be processed, combined, arranged, and/or presented in many other ways.

User 101 and/or automated data input devices or programs (not shown) may provide data related to the design or conduct of experiments. As one further non-limiting example related to the processing of an Affymetrix GeneChip® probe array, the user may specify an Affymetrix catalogue or custom chip type (e.g., GeneChip® Mapping 500 K Array Set) either by selecting from a predetermined list presented by GCOS or by scanning a bar code, Radio Frequency Identification (RFID), or other means of electronic identification related to a chip to read its type. GCOS may associate the chip type with various scanning parameters stored in data tables including the area of the chip that is to be scanned, the location of chrome borders on the chip used for auto-focusing, the wavelength or intensity/power of excitation light to be used in reading the chip, and so on. As noted, applications 272 may apply some of this data in the generation of intermediate results. For example, information about the dyes may be incorporated into determinations of relative expression.

Those of ordinary skill in the related art will appreciate that one or more operations of applications 272 may be performed by software or firmware associated with various instruments. For example, scanner 100 could include a computer that may include a firmware component that performs or controls one or more operations associated with scanner 100.

Web Server 120: An example of web server 120 is illustrated in FIGS. 1 and 2 and may support one or more web sites or "portals" accessible remotely by computers, handheld devices, cell phones, or other web capable devices known in the art via network 125. Typical embodiments of server 120 may include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes, and other known devices or media and those that may be developed in the future. The computer executable instructions may be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Baxevanis Bioinformatics: A Practical Guide for Analysis of Gene and Proteins (Wiley & Sons, Inc., 2nd ed., 2001).

As will be appreciated by one of skill in the art, the present invention may be embodied as a method, data processing system or program products. Accordingly, the present invention may take the form of data analysis systems, methods, analysis software, and so on. Software written according to the present invention typically is to be stored in some form of computer readable medium, such as memory, or CD-ROM, or transmitted over a network, and executed by a processor. For a description of basic computer systems and computer networks, see, e.g., Introduction to Computing Systems: From Bits and Gates to C and Beyond by Yale N. Patt, Sanjay J. Patel, 1st edition (Jan. 15, 2000) McGraw Hill Text; ISBN: 0072376902; and Introduction to Client/Server Systems: A Practical Guide for Systems Professionals by Paul E. Renaud, 2nd edition (June 1996), John Wiley & Sons; ISBN: 0471133337, both of which are hereby incorporated by reference for all purposes.

Computer software products may be written in any of various suitable programming languages, such as C, C++, Fortran and Java (Sun Microsystems). The computer software product may be an independent application with data input and data display modules. Alternatively, the computer software products may be classes that may be instantiated as distributed objects. The computer software products may also be component software such as Java Beans (Sun Microsystems), Enterprise Java Beans (EJB), Microsoft® COM/DCOM, etc.

Web Server 120 is illustrated in FIGS. 1 and 2 as a single computer platform or machine, but those of ordinary skill in the related art will appreciate that web server 120 may comprise one or more server platforms, and may typically comprise a plurality of server machines.

Figure 3:
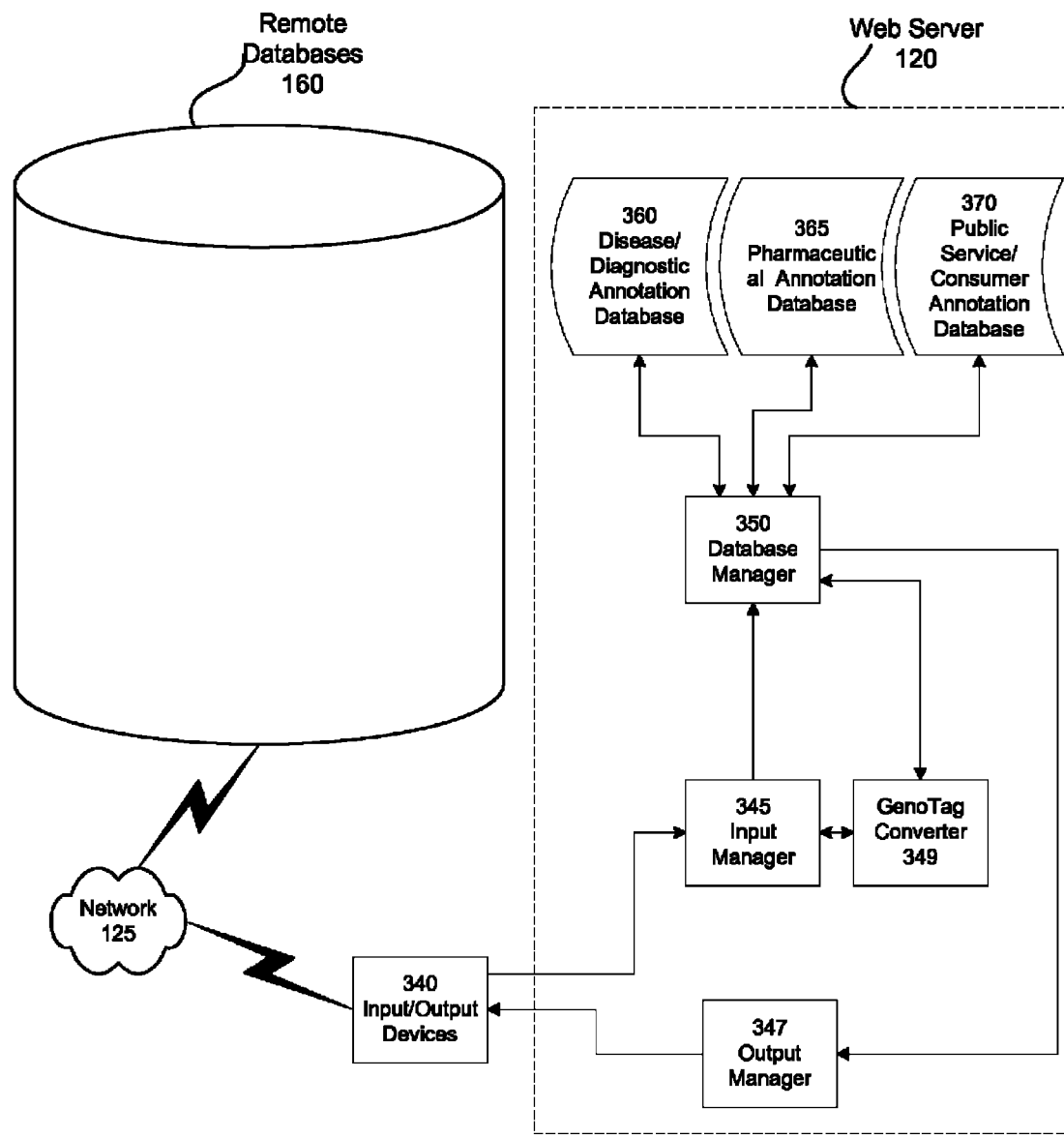
FIG. 3 is a functional block diagram of one embodiment of the web server and remote databases of FIG. 1, wherein the web server comprises an input manager, an output manager, a database manager, and a GenoTag converter.

Illustrative examples of functional elements associated with server 120 as illustrated in FIG. 3, such as database manager 350, input and output managers 345 and 347. That is, in a typical implementation, the functions of managers 345 and 347 are carried out by the execution of software applications on and across one or more computer platforms represented by server 120. In the illustrated embodiment, database manager 350 coordinates the storage, maintenance, supplementation, and all other transactions from or to any local databases. Manager 350 may undertake these functions in cooperation with appropriate database applications such as the Oracle® 10g database management system available from Oracle of Redwood Shores Calif.

For example, server 120 may be any type of known computer platform or a type to be developed in the future, although typically will be of a class of computer commonly referred to as servers. However, server 120 may also be a main frame computer, a work station, or other computer type. Server 120 may be connected via any known or future type of cabling or other communication system including wireless systems, either networked or otherwise. Various computing elements of server 120 may be co-located or they may be physically separated. Various operating systems may be employed on any of the computer platforms, possibly depending on the type and/or make of computer platform chosen. Appropriate operating systems include Windows NT®, Sun Solaris, Linux, OS/400, Compaq Tru64 Unix, SGI IRIX, Siemens Reliant Unix, and others.

There may be significant advantages to carrying out the functions of server 120 on multiple computer platforms, such as lower costs of deployment, database switching, or changes to enterprise applications, and/or more effective firewalls. Other configurations, however, are possible. For example, as is well known to those of ordinary skill in the relevant art, so-called two-tier or N-tier architectures are possible, See, for example, E. Roman, Mastering Enterprise JavaBeans™ and the Java™2 Platform (Wiley & Sons, Inc., NY, 1999) and J. Schneider and R. Arora, Using Enterprise Java™ (Que Corporation, Indianapolis, 1997), both of which are hereby incorporated by reference in their entireties for all purposes.

It will be understood that many hardware and associated software or firmware components that may be implemented in a server-side architecture for Internet commerce may be included, as well as components to implement one or more firewalls to protect data and applications, uninterruptible power supplies, LAN switches, web-server routing software, and many other components. Similarly, a variety of computer components customarily included in server-class computing platforms, as well as other types of computers, will be understood to be included but are not shown. These components include, for example, processors, memory units, input/output devices, buses, and other components noted above with respect to user computer 100. Those of ordinary skill in the art will readily appreciate how these and other conventional components may be implemented.

The functional elements of server 120 also may be implemented in accordance with a variety of software facilitators and platforms (although it is not precluded that some or all of the functions of server 120 may also be implemented in hardware or firmware). Among the various commercial products available for implementing e-commerce web portals are BEA WebLogic from BEA Systems, which is a so-called "middleware" application. This and other middleware applications are sometimes referred to as "application servers". The function of these middleware applications generally is to assist other software components to share resources and coordinate activities. The goals include making it easier to write, maintain, and change the software components; to avoid data bottlenecks; and prevent or recover from system failures. Thus, these middleware applications may provide load-balancing, fail-over, and fault tolerance, all of which features will be appreciated by those of ordinary skill in the relevant art.

Other development products, such as the Java™ 2 platform from Sun Microsystems, Inc. may be employed in server 120 to provide suites of applications programming interfaces (API's) that, among other things, enhance the implementation of scalable and secure components, examples of API's for use with probe array related information and architectures may be found in U.S. Pat. No. 6,954,699, which is hereby incorporated by reference herein in its entirety for all purposes. The platform known as J2EE (Java™2, Enterprise Edition), is configured for use with Enterprise JavaBeans™, both from Sun Microsystems. Enterprise JavaBeans™ generally facilitates the construction of server-side components using distributed object applications written in the Java™ language. Thus, in one implementation, the functional elements of server 120 may be written in Java and implemented using J2EE and Enterprise JavaBeans™. Various other software development approaches or architectures may be used to implement the functional elements of server 120 and their interconnection, as will be appreciated by those of ordinary skill in the art Some embodiments of web server 120 may perform one or more methods for providing personalized genotype based information in response to one or more queries, and more specifically genotype based information personalized for individuals based upon genotype calls generated using biological probe arrays. The queries may typically be received and information returned to users over network 125 such as the Internet as described in U.S. patent application Ser. Nos. 10/063,559, 10/065,856; 10/065,868; 10/197,621; 10/328, 872; 10/328,818; 10/423,403; 10/903,344; and 10/903,641; U.S. Provisional Patent Application Ser. Nos. 60/748,884; and 60/759,090, which are all hereby incorporated by reference herein in their entireties for all purposes.

In some embodiments, user 101 may provide one or more "search terms" to server 120 for processing using internet client 279 that enables user 101 to communicate via one or more GUI's 246. Server 120 may then return various types of customized information in response to particular request by user 101. In particular the information may be customized based upon genotype information associated with user 101 or another individual of interest. Those of ordinary skill in the related art will appreciate that inputs to server 120 by user 101 are not necessarily limited to search terms, rather search terms provide a useful means to obtain customized genotype based information. For example, customized genotype based information may be associated with a user selection of results from a previous search. In the present example, user 101 may select a class of drug identified from the results of a search performed, where the information provided in response may includes drugs that are known to be effective based upon user 101's genotype profile. Such information may include advertisements, product information literature, efficacy information, scientific literature or publications, or other personalized information that may be useful to user 101.

Various types of customized genotype based information returned to user 101 may pertain to what may be referred to as personalized medicine including associations with disease conditions, diagnostic products and/or services, pharmaceutical products and/or related information, and other associated information. For example, in response to a user selection of one or more search terms, server 120 provides user 101 with associated personalized information that may include one or more of diagnostic, pharmaceutical, advertising, or other descriptive information. In the same or alternative example, the search terms may be intended to produce a certain class of intended result where server 120 may also return additional personalized information that may be of interest to user 101. Server 120 may determine that the information may be of interest using some combination of the search terms and genotype data associated with user 101. The information of interest may include advertising, public service announcements, consumer reports, or other type of information. This information may be helpful to user 101 in choosing appropriate products and/or services based upon personalized genotype based criteria.

Some embodiments of the present invention employ personalized genotype based information. Examples of genotype based information include the identification of one or more SNP's, genome sequence information, or some combinations thereof. There are a number of methods known in the art for generating sequence based information such as gel based sequencing (i.e. employing the Maxum-Gilbert, or Sanger methods), capillary electrophoresis based methods that employ fluorescent detection to make base calls, or other sequencing methods known in the art. It may be preferable in some embodiments to employ high throughput sequencing methods that offer the advantages of low cost and wide genome coverage. Such methods may, for example, include embodiments of probe arrays 140 that offer genome wide coverage and detection of SNP's or sequence composition. For example, the GeneChip® Mapping 500 K Array Set provides genome-wide coverage of 500,000 SNP's. An individual's genotype for each of the SNP's may be determined in a single experiment at a low cost and more efficiently in comparison to other genotyping methods. In the present example, each of the SNP calls may be output in a computer generated file amenable to further processing.

Figure 4:
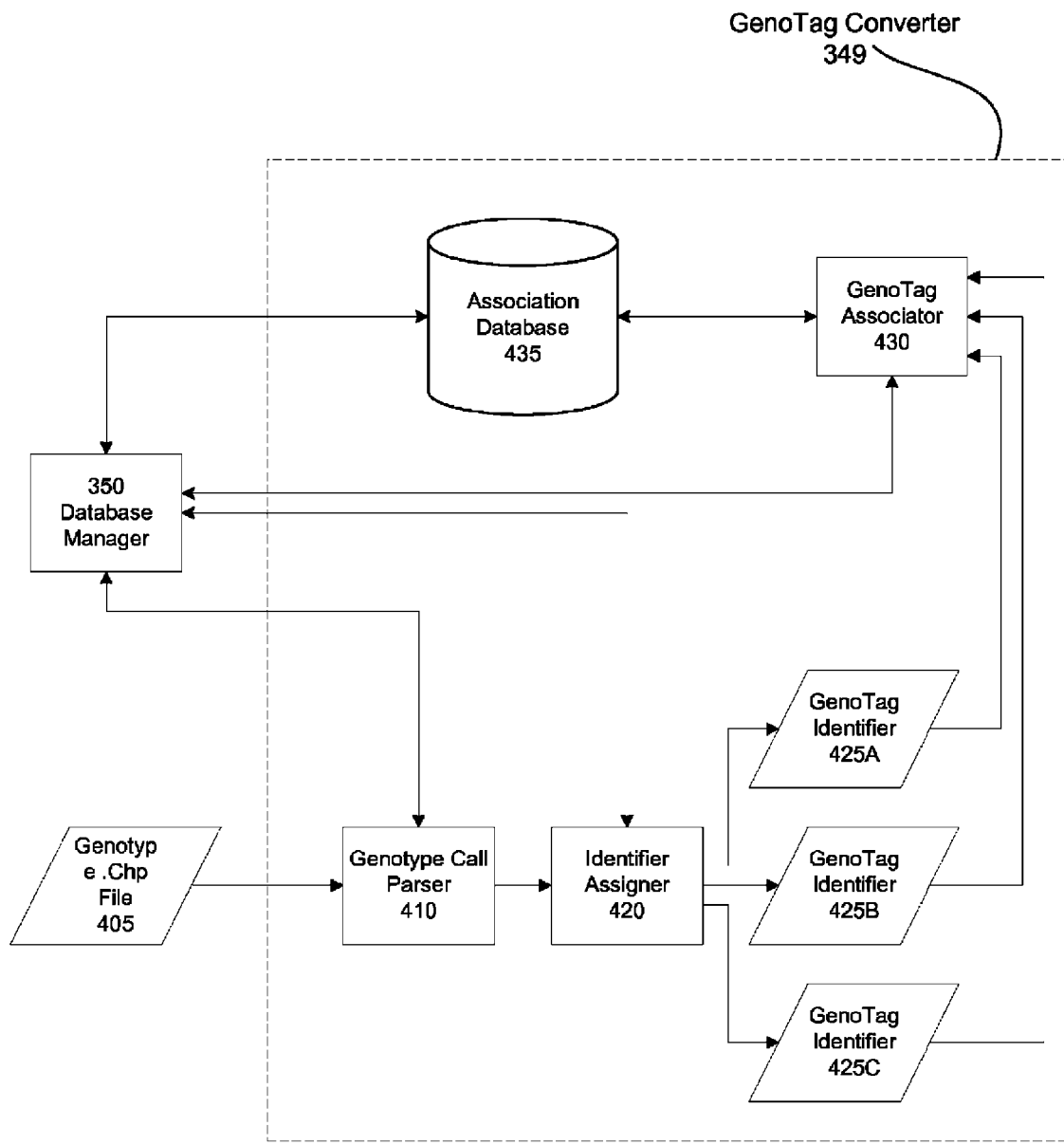
FIG. 4 is a functional block diagram of one embodiment of the GenoTag converter of FIG. 3 that assigns one or more GenoTag identifiers to represent genotype calls.

Some embodiments of server 120 may include a means to convert genotype calls into an electronic identifier readable by one or more software elements. For example, FIG. 4 provides an illustrative example of elements associated with GenoTag converter 349 that covert one or more genotype calls stored in genotype .chp file 405 into electronically identifiable elements that may be referred to as GenoTags. In the present example, genotype .chp file 405 may include all genotype calls associated with an experiment performed using an embodiment of probe array 140. As illustrated in the example of FIG. 4, genotype call parser 410 may receive genotype .chp file 405 and extract one or more individual genotype calls for conversion.

Parser 410 may in some embodiments extract some or all of the genotype calls associated with file 405 based upon the relevance of calls and other criteria. Identification and number of genotype calls identified for extraction may be user selectable, determined by database manager 350 or other software elements using the state of knowledge associated with genotype calls (i.e. association with characteristics or disease profiles), particular disease or diagnosis associations, or other criteria useful in the art. Also, some genotype calls associated with file 450 may include what is referred to as a "no call", where for various reasons a definitive call was not made for an associated probe set. Since a "no call" genotype call does not identify SNP or sequence composition it does not have utility for identifying personalized information, and may be desirable in some embodiments to exclude all no calls in further processing operations. For example, it may be computationally expensive and an inefficient use of data storage to convert and store all genotype calls in file 405 if only a subset of calls is relevant to a user's interest or useful given the state of knowledge. Alternatively, it may desirable to convert all genotype calls associated with file 450 in a single process that may be employed for the individual in all future uses of the GenoTags. In the present example, a user may submit their DNA to be genotyped using one or more probe arrays 140 and subsequently have every genotype call converted to a GenoTag format. The GenoTag format may represent positional information in the genome as well as genotype composition that may include SNP or nucleic acid identity for a position in the genome. For instance positional information could include a chromosome identifier and a positional identifier on said chromosome associated with the genotype call. In some embodiments Boolean or binary representations may be employed to represent SNP composition, such as for instance, wild type versus mutant type identification. Typically, the GenoTags may not include annotations such as for disease or diagnostic applications due to the dynamic nature of scientific progress. In other words, a particular GenoTag identifier may indicate an individuals' genotype for a particular SNP but the state of knowledge with respect to that SNP may change over time. It may be desirable to dynamically associate the GenoTag identifier with information of interest using the most up to date information available for the relevant genotype calls. Alternatively, association updates may occur at regular intervals, stored in precompiled files or databases. In some situations using precompiled information may be less computationally complex than performing associations with every query while efficiently providing high quality information.

In the example illustrated in FIG. 4, parser 410 forwards the extracted genotype call information to identifier assigner 420 for assignment of GenoTag identifiers. For each genotype call, assigner 420 may assign one or more electronically identifiable GenoTags. An electronically identifiable GenoTag may comprise various formats, and data storage solutions. For example, a GenoTag format may include a text file or a string of characters. Those of ordinary skill in the art will appreciate that software such as database manger 350 may employ various programming languages such as Perl that are enabled for Regular expression searching that can identify strings of one or more characters in text. Alternatively the structure of the text file or string of characters is defined such that elements such as database 350 may easily identify the correct information by looking in the correct part of the defined structure.

Alternatively, some embodiments of a GenoTag format could include an HTML or XML type file that is platform independent and amenable to application by software elements commonly employed such as internet client 279. For example, an XML file may be generated comprising a structure that effectively represents the information encoded by the GenoTag. In the present example, assigner 420 may assign a file name to each XML file that include some or all of the elements of the GenoTag that uniquely identify the file for easy searching. Alternatively, assigner 420 may assign a different type of identifier as a file name that may be more amenable to various applications such as a relational database structure.

As described above, identifier assigner 420 may assign one or more GenoTag identifiers using one or more formats for each genotype call, outputting GenoTag identifiers 425 (represented as 425A, 425B, and 425C). In the presently described example, each of GenoTag identifiers 425 may be received by GenoTag associator 430 that in some embodiments associates each GenoTag with information of interest. In addition, associator 430 may associate one or more search terms or other terminology and language that may be employed in various searches with each of GenoTag identifiers 425.

In some embodiments associator 430 may employ one or more of disease/diagnostic annotation database 360, pharmaceutical annotation database 365, or public service/consumer annotation database 370 as a local source of the information of interest. Alternatively, associator 360 may employ remote sources such as remote databases 160 to acquire some or all of the desired information. Typically, it would be desirable that each of databases 360, 365, and 370 be regularly updated by database manger 350 with information from remote databases 160. For example, database manager 350 may update one or more of databases 360, 365, or 370 according to any chronological schedule (e.g., daily, weekly, etc.), or need-driven schedule (e.g., in response to a user making an authorized request for updated information), manager 350 may, in accordance with known techniques, initiate searches of remote databases 160 by formulating appropriate queries, addressed to the URL's of the various databases 160, or by other conventional techniques for conducting data searches and/or retrieving data or documents over the Internet. These search queries and corresponding addresses may be provided in a known manner to output manager 347 for presentation to databases 160. Input manager 345 receives replies to the queries and provides them to manager 350 for updating of database 360, all in accordance with any of a variety of known techniques for managing information flow to, from, and within an Internet site. Alternatively, in some embodiments updates to annotation database 360 may be performed manually by an operator employing one or more computers of server 120, where for instance the process of curating the data may require manual interventions by the operator, where the curated data may be subsequently uploaded to database 360.

In some embodiments, associator 430 may generate a "look-up" table comprising rows and tuples that references each GenoTag with information of interest. The nature of the association may be based upon information represented by the GenoTag. For example, one or more GenoTags may represent an individuals' sensitivity to a particular drug based upon the individuals' genotype calls, where it may be recommended that the individual avoid the drug. The association with the drug as information of interest in the look-up table with the GenoTag may include an identifier that signifies that the drug is not recommended for the individual. Thus, when a software element such as database manager 350 performs a search for drugs for the individual, manager 350 will return a result that indicates that the drug is not recommended or alternatively not return the drug in the results. For instance, in certain applications such as advertising it would not be advisable to advertise a drug that is not recommended for the individual. Also in the present example, each of identifiers 425 may be stored in a memory such as system memory 270 or memory storage devices 281 where the storage location may be referenced in the look-up table so that each identifier 425 may be quickly located and accessed. In the same or alternative embodiments, associator 430 may employ a relational database, or other type of data structure to perform all of the association, reference and storage functions.

In the same or alternative embodiments, associator may also determine a relative rank of importance with respect to the association between one or more GenoTags and the information of interest. For example, associator 430 may assign a rank for each association between a GenoTag and information of interest where the rank may be representative of the quality of the information of interest that reflects upon the strength of association (i.e. low quality information infers a weak or low ranked association). The rank may also represent the strength of association. For instance, a genotype associated with a GenoTag may have an inferred but not proven association with information of interest and thus the strength of association may be weak relative to a proven association. In the same or alternative embodiment, associator 430 may also determine ranking for groups of two or more GenoTags that may be referred to as a "GenoTag Signature". For instance, groups of two or more genotype calls each represented by a GenoTag may be related with respect to one or more instances of information of interest. Associator 430 may determine a rank in similar manner as described above with respect to single GenoTags.

As noted, one of the functional elements of server 120 is input manager 345. Manager 345 receives a set, i.e., one or more, of search terms or other type of terminology from user 101 over network 125. These functions are performed in accordance with known techniques common to the operation of Internet servers, also commonly referred to in similar contexts as presentation servers. For example, database manager 350 may perform one or more searches to generate a set of results based upon the search criteria. In the present example, such searches may be performed using methods commonly known it the related art. In some embodiments, the search may be performed by search "engines" provided by third parties such as the well known Google search engine provided by Google of Mountain View Calif., Yahoo search engine provided by Yahoo!, Inc. of Sunnyvale Calif., or other search engines currently available or that may be developed in the future. Database manager 350 may customize the results of a search returned based upon an individuals genotype represented by the GenoTags. For instance, database manager 350 may eliminate some results using an association determined using the GenoTags. Alternatively, database 350 may identify some results as information of interest to user 101 using the association of GenoTags.

Another of the functional elements of server 120 is output manager 347. Manager 347 provides information such as web page 210 to user 101 over network 125 for presentation in one or more of GUI's 246, also in accordance with those known techniques. The presentation by manager 347 of data may be implemented in accordance with a variety of known techniques. As some examples, data may include HTML or XML files, email or other files, or data in other forms. The data may include Internet URL addresses so that user 101 may retrieve additional HTML, XML, or other documents or data from remote sources that could include information stored in remote databases 160.

Some embodiments that include GenoTag identifiers 425 associated with user 101 may require user 101 to "login" to a server or software application in order to properly identify the GenoTags associated with user 101. In some cases, what are generally referred to as "cookies" or HTTP cookies may be employed to store one or more GenoTags on a user computer, thus avoiding the need for user 101 to identify themselves. For example, a genotyping service provider may employ server 120 to process the genotyping results as described above. User 101 may initially login to server 120 using internet client 279 to see the results and use various services provided by the service provider. Server 120 may store one or more cookies each comprising one or more GenoTags in system memory 270 of computer 150 or other computer employed by user 101. In the present example, user 101 may select the GenoTags to be represented by the cookies or they may be defined by database manager 350 using one or more criteria. User 101 may subsequently employ computer 150 to search using server 120, or other remote computing architectures that support searching and are enabled to identify and use GenoTags. Thus, server 120 or any other enabled computing architecture may receive the GenoTags from computer 150 without user 101 performing a login step or other active steps. The receiving computing structure may employ the GenoTags to filter results produced from user queries to return personalized results to computer 150 based upon user 101s' genotype.

Associations of genotype or genetic sequence to various human traits and conditions are resulting from research studies enabled by the completion of the sequencing of the human genome. Direct-to consumer genotyping services offer individuals the ability to obtain their own genetic data, whether in the form of SNP genotyping or more comprehensive genome and/or mitochondrial DNA sequencing. The invention described herein outlines the process of enabling electronic linkage of genotype or sequence data to known genetic associations.

Genotype or sequence data that has been generated for an individual on any platform or technology can be stored in a database. Each genotype call or sequence datapoint for that individual is then assigned an electronic tag (for example, XML), creating a new field in the dataset with this code, or GenoTag. The GenoTag, or a set of GenoTags (called a GenoTag Signature), is then available for use as an electronic identifier during internet searches or other data mining purposes including, but not limited to, the following applications. Each GenoTag can be a modular piece of information that represents one particular piece of genetic information, such as a numerical indicator for person, SNP, and genotype. These bits of information may be presented without further genetic information, such as surrounding nucleic acid sequence.

The methods of the invention are particularly well suited for online advertising and connection between a subject or consumer and vendors of products or services targeted to particular genotypes. The present invention can also be useful in predictive diagnostics, novel therapeutics, nutritional therapies and community related information transmission for people with similar genotypes.

The relevance of online advertising is facilitated by a consumer's genotype data. Look-up tables are created that link specific search terms to GenoTags. When a search term is typed into a search window, whether on the world wide web or in a proprietary environment, it is automatically compared against the look-up table for associated GenoTags. These GenoTags are then transmitted when the search is conducted. Intercepting organizations or databases automatically pick up these tags during the internet search and the search results are ranked based on best fit to the GenoTag profile.

Another preferred embodiment is to provide a test to market specific foods, supplements or drugs based on the genotype of the subject. Using nutritional needs as a phenotype, a user of the method could determine nutrition requirements as a function of genotype. Also, one preferred embodiment includes the development of specific drugs based on the genotype of the subject. A user of the method could also use drug response as a phenotype, and then use the above to determine drug use as a function of genotype, and make a selection of drug, drug dose or drug combinations.

Data for any of the present methods can be provided by PUSH technology over the Internet, by e-mail to the user, through a web site or web page that the user accesses from PC, a communications network, cellphone or other device, or physical mail sent to the user. The present invention includes any convenient way to connect a user of the method with the information.

Another preferred embodiment comprises the following sequence of procedures; a person registers their IP address and GenoTags into a proprietary environment; when the person searches for any search term on the web, an automatic search for relevant advertising is also performed automatically; search terms are matched with products using the aforementioned product database (a database that links search terms to consumer products).

In the pharmaceutical industry, the present invention has utility for pharmaceutical companies to market drugs to appropriate individuals. As genetic markers for positive (or negative) response to drugs are generated, these data are converted into GenoTags, which can then be used to filter search results when consumers (or their doctors) are investigating which drugs to use for a given indication, either through searches of public databases or proprietary databases. GenoTags, in this scenario, would be used to tailor treatment, such as the delivery of personalized medicine. Users can also perform searches and discover genotypes that would benefit from a particular drug or therapy and communicate that information to persons having that genotype.

One preferred embodiment comprises the following sequence of procedures; a consumer registers their IP address and GenoTag into a proprietary environment; a consumer searches for information on a disease which has a GenoTag; a product database which links GenoTags, disease, and treatments is created; and the treatment that is appropriate for that GenoTag is ranked highest in the search results.

Another preferred embodiment comprises the following sequence of procedures; a consumer registers their IP address and GenoTag into a proprietary environment; a consumer searches for information on a disease which has a GenoTag; a product database which links GenoTags, disease, and treatments is created; the treatment that is not appropriate for that GenoTag is indicated in the search results.

Another preferred embodiment comprises the following sequence of procedures; a consumer registers their IP address and GenoTag into a proprietary environment; a consumer searches for information on a subject of interest, such as clothing, product, location, allergies, which will be matched to their GenoTag; and an online marketing software will select products or services which are compatible or desirable for that genotype. It will present the search results and rank them in order of an automatic or customized list of preferences.

In the clinical setting, disease diagnosis could also be facilitated using GenoTags. Once disease signatures are identified, the genetic information is tagged to pull out the associated GenoTags located in an individual's genetic dataset. If there is a match, the individual is notified that they may have predisposition to a disease (if they choose to be given the information). Then appropriate recommendations may follow, for treatments, drug therapies or interactions, physical health specialists, and any other product or service appropriate for that disease.

One preferred embodiment comprises the following sequence of procedures; a consumer has their genome genotyped; the resulting genotype information is compared against a database of GenoTags that are associated with particular diseases; if there is a match, the consumer is notified that they have the disease based on their GenoTag.

Another preferred embodiment comprises the following sequence of procedures; a consumer has their genome genotyped; the resulting genotype information is compared against a database of GenoTags that are associated with particular diseases; if there is not a match, the consumer is notified that they do not have the disease based on their GenoTag.

In the social setting, networking could also be facilitated using GenoTags. GenoTags could be used to suggest connections among individuals or to suggest that certain connections be avoided. Suggested connections could be for the use of social dating, support network for disease management, or used for community involvement.

One preferred embodiment comprises the following sequence of procedures; a consumer registers their IP address and GenoTags into a proprietary environment; a consumer searches for individuals with similar GenoTags, such as GenoTags associated with obesity; the search results contain contact information for individuals with the obesity GenoTag thereby facilitating networking.

In the research setting, sample recruitment could also be facilitated using GenoTags. Individuals that have registered their GenoTags could be queried by physicians that need samples for clinical trials or researchers that need samples to study the disease. Subjects can be notified via a website of an opportunity to participate in a study of a specific trait. The results can be shared back with the community and the process can be made interactive with data sharing in the database concerning any trait, infection, and/or disease.

One preferred embodiment involves a subscription, where health information is provided to the user based on their GenoTag. The GenoTag of a subject can be obtained either by being entered by the user, retrieved from the user's computer, or obtained from an online database. Health information can be delivered to the user with the trait whenever there is new health information is obtained for that GenoTag or trait. A user's account may be automatically debited periodically for participation in the service. Other payment options may be employed.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A computer-implemented method of using information about an individual's genotype to select products and services for that individual, comprising:
receiving a plurality of genotype calls for a plurality of polymorphisms, wherein each genotype call identifies the individual's genotype at each polymorphism;
assigning a plurality of genotag identifiers for each genotype call, wherein the plurality of genotag identifiers comprises an identifier of chromosome, an identifier of genomic position and an identifier of the genotype call, wherein the plurality of genotag identifiers does not comprise nucleic acid sequence data, and wherein the plurality of genotag identifiers is electronically identifiable, readable by computer softwares, and stored in a storage database;
associating in a relational database, each genotag identifier with information from a plurality of dynamic databases, thereby producing a plurality of associated genotag identifiers, wherein the plurality of dynamic databases comprises a first database containing information about disease diagnostics, a second database containing information about pharmaceuticals and a third database containing consumer information, and wherein the plurality of dynamic databases is updated in accordance with a a schedule;
determining a relative ranking of each associated genotag identifier, wherein the ranking is indicative of information quality or association strength;
generating a set of search results in response to a search initiated by a user over a data network, wherein the search comprises using at least one of the associated genotag identifiers, wherein the set of search results are ranked using the relative ranking, thereby providing search results customized for the individual; and
outputting to the user the set of search results from the generating step, wherein all steps of the method are performed on a computer.

2. The method of claim 1, wherein the genotype calls are generated by hybridization of a genomic sample from the individual to a biological probe array.

3. The method of claim 1, wherein the search results are used by the user to select products or services for the individual.

4. The method of claim 3, wherein the individual's genotag identifiers are transmitted over a data network to provide a match to select the products or services.

5. The method of claim 3, wherein the individual's genotag identifiers are transmitted over a network to provide a match to select the products or services based on criteria such as phenotype, genotype, physical condition, qualities, traits, diseases, states, gene data, expression or protein information, location, community information, interests, habits, preferences, and allergies.

6. A computer-implemented method to automatically match genotyping information to information about commercial products or services and to provide the information about commercial products or services to a user as a list of search results, comprising:
obtaining a plurality of genotype calls from an individual wherein each genotype call identifies the genotype of the individual at a polymorphism;
assigning a plurality of genotag identifiers to the plurality of genotype calls by means of a computer, wherein each genotag identifier is an electronic tag indicative of a fixed characteristic of each genotype call, and wherein each genotag identifier does not comprise nucleic acid sequence data;

storing the plurality of genotag identifiers in a first database;

using a computer processor to match at least one of the plurality of genotag identifiers in the first database to commercial products or services in response to a search initiated by the user over a data network, wherein the at least one genotag identifier is compared to a second database of search terms associated with characteristics of individuals, thereby obtaining search results; and outputting the search results to the user.

7. A method in accordance with claim 6, wherein the second database comprises a disease diagnostic annotation database, a pharmaceutical annotation database and a public service annotation database.

8. A method in accordance with claim 6, wherein the database of search terms comprises terms associated with characteristics of individuals selected from the following: phenotype, genotype, physical condition, qualities, traits, diseases, states, gene data, expression or protein information, location, community information, interests, habits, preferences, and allergies.

9. A method in accordance with claim 7, wherein drug treatment is recommended based on the search results.

10. A system to automatically match genotyping information to commercial products or services, comprising:

a computer having a processor and a memory coupled to the processor to store a plurality of genotype calls derived from an individual, wherein each genotype call is associated with a different polymorphism and is indicative of the individual's genotype at that polymorphism;

computer instructions for assigning a plurality of genotag identifiers for each genotype call, wherein each genotag identifier is electronically identifiable and an indicator of a physical feature of the polymorphism associated with the genotype call, and wherein genotag identifier does not comprise nucleic acid sequence data;

an associator to match the plurality of genotag identifiers with information or search terms in a database of information or search terms associated with characteristics of individuals based on genotype, wherein the information in the database is dynamic and is updated at least weekly;

computer instructions for matching the information or search terms matched with the plurality of genotag identifiers to commercial products or services in response to a search initiated by the user over a network; and a computer configured for providing a list of search results to the user.

11. The method of claim 1, further comprising recommending to the individual, social connections with one or more different individuals in a network, based on a predicted common interest, wherein the individual's genotag identifiers are used to predict common interest.

12. The method of claim 1, further comprising recommending to the individual, social connections with one or more different individuals in a network, based on a predicted common interest in disease management, wherein the individual's genotag identifiers are used to predict common interest in disease management.

13. The method of claim 1, further comprising recommending to the individual, social connections with one or more different individuals in a network, based on a predicted common interest in involvement in a particular community, wherein the individual's genotag identifiers are used to predict common interest in involvement a particular community.

14. The method of claim 1, wherein the search results are provided to the user by electronic mail over the Internet.

15. The method of claim 1, wherein the search results are provided to the user by cellular phone.

16. The method of claim 2, wherein the biological probe array comprises probes for genotyping 500,000 single nucleotide polymorphisms.

17. The method of claim 1, further comprising combining a plurality of genotag identifiers to form a signature and assigning an electronic identifier to the signature.

18. The method of claim 1, wherein the genotag identifiers and the user's IP address are registered in a proprietary environment.

19. The method of claim 14, wherein the search results are provided to the user as an electronic mail using PUSH technology.

20. The method of claim 15, wherein the search results are provided to the user by PUSH technology.

* * * * *